(12) United States Patent
Song et al.

(10) Patent No.: US 9,265,856 B2
(45) Date of Patent: Feb. 23, 2016

(54) MULTIPLE COMPONENT MATERIALS HAVING A COLOR-CHANGING COMPOSITION

(75) Inventors: Xuedong Song, Alpharetta, GA (US); Thomas M. Ales, III, Neenah, WI (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 0 days.

(21) Appl. No.: 12/825,877

(22) Filed: Jun. 29, 2010

(65) Prior Publication Data

US 2011/0015599 A1 Jan. 20, 2011

Related U.S. Application Data

(63) Continuation-in-part of application No. 12/503,364, filed on Jul. 15, 2009, now abandoned, and a continuation-in-part of application No. 12/503,380, filed on Jul. 15, 2009, now abandoned.

(51) Int. Cl.
| | |
|---|---|
| *G01N 21/75* | (2006.01) |
| *A61L 15/56* | (2006.01) |
| *A61F 13/42* | (2006.01) |
| *C09B 7/00* | (2006.01) |
| *G01N 31/22* | (2006.01) |
| *G01N 33/566* | (2006.01) |
| *G01N 21/78* | (2006.01) |
| *G01N 33/84* | (2006.01) |
| *G01N 21/81* | (2006.01) |
| *G01N 21/29* | (2006.01) |
| *G01N 33/52* | (2006.01) |
| *G01N 33/543* | (2006.01) |
| *G01N 21/80* | (2006.01) |
| *G01N 21/84* | (2006.01) |

(52) U.S. Cl.
CPC .............. *A61L 15/56* (2013.01); *A61F 13/42* (2013.01); *C09B 7/00* (2013.01); *G01N 21/29* (2013.01); *G01N 21/78* (2013.01); *G01N 21/80* (2013.01); *G01N 21/81* (2013.01); *G01N 21/8483* (2013.01); *G01N 31/22* (2013.01); *G01N 31/222* (2013.01); *G01N 33/525* (2013.01); *G01N 33/54386* (2013.01); *G01N 33/566* (2013.01); *G01N 33/84* (2013.01); *Y10T 428/2481* (2015.01); *Y10T 428/24802* (2015.01)

(58) Field of Classification Search
CPC ....... G01N 33/84; G01N 21/78; G01N 21/80; G01N 21/81; G01N 21/8483; G01N 31/22; G01N 33/525; G01N 21/29; G01N 31/222; G01N 33/54386; G01N 33/566
USPC ........... 422/400, 420; 436/164, 169; 604/358, 604/361
See application file for complete search history.

(56) References Cited

U.S. PATENT DOCUMENTS

| | | | |
|---|---|---|---|
| 4,022,211 A | 5/1977 | Timmons et al. | |
| 4,231,370 A | 11/1980 | Mroz et al. | |
| 4,287,153 A | 9/1981 | Towsend | |
| 4,895,567 A | 1/1990 | Colon et al. | |
| 4,931,051 A | 6/1990 | Castello | |
| 5,035,691 A | 7/1991 | Zimmel et al. | |
| 5,167,652 A | 12/1992 | Mueller | |
| 5,302,654 A | 4/1994 | Ishii et al. | |
| 5,464,470 A | 11/1995 | Brachman et al. | |
| 6,121,365 A | 9/2000 | Saibara et al. | |
| 6,121,509 A | 9/2000 | Ashraf et al. | |
| 6,710,221 B1 | 3/2004 | Pierce et al. | |
| 6,756,520 B1 * | 6/2004 | Krzysik et al. ................ | 604/360 |
| 6,772,708 B2 | 8/2004 | Klofta et al. | |
| 6,855,434 B2 | 2/2005 | Romasn-Hess et al. | |
| 6,904,865 B2 | 6/2005 | Klofta et al. | |
| 7,005,557 B2 * | 2/2006 | Klofta et al. .................. | 604/360 |
| 7,094,464 B2 | 8/2006 | Mao et al. | |
| 7,159,532 B2 * | 1/2007 | Klofta et al. .................. | 116/206 |
| 7,306,764 B2 | 12/2007 | Mody | |
| 7,332,642 B2 * | 2/2008 | Liu ................................ | 604/361 |
| 2002/0155281 A1 | 10/2002 | Lang et al. | |
| 2005/0092204 A1 | 5/2005 | Zhu et al. | |
| 2005/0112151 A1 | 5/2005 | Horng | |
| 2005/0234414 A1 | 10/2005 | Liu | |
| 2005/0234415 A1 | 10/2005 | Liu | |
| 2006/0229578 A1 | 10/2006 | Roe et al. | |
| 2007/0002072 A1 | 1/2007 | Frensch et al. | |
| 2007/0079748 A1 | 4/2007 | Ahmed | |
| 2007/0100305 A1 | 5/2007 | Isogai et al. | |
| 2008/0068399 A1 | 3/2008 | Goss et al. | |
| 2009/0157025 A1 | 6/2009 | Song et al. | |
| 2009/0275908 A1 | 11/2009 | Song | |
| 2011/0015063 A1 | 1/2011 | Gil et al. | |
| 2011/0015597 A1 | 1/2011 | Gil et al. | |
| 2011/0015598 A1 | 1/2011 | Song et al. | |

FOREIGN PATENT DOCUMENTS

| | | | |
|---|---|---|---|
| JP | 2006326221 A | * | 12/2006 |
| KR | 10-1996-0014278 A | | 5/1996 |
| KR | 10-2007-0083314 A | | 8/2007 |
| KR | 10-2009-0061633 A | | 6/2009 |
| KR | 10-2009-0074223 A | | 6/2009 |
| WO | WO 95/16562 A1 | | 6/1995 |
| WO | WO 99/33651 A1 | | 7/1999 |
| WO | WO 02/36177 A2 | | 5/2002 |
| WO | WO 03/051250 A1 | | 6/2003 |
| WO | WO 2008/038654 A1 | | 4/2008 |
| WO | WO 2009/141684 A1 | | 11/2009 |

* cited by examiner

*Primary Examiner* — Dennis M White
(74) *Attorney, Agent, or Firm* — Kimberly Clark Worldwide Inc.

(57) ABSTRACT

The present invention relates to a multiple-component material including a substrate and a printed layer on the substrate. The printed layer includes a color-changing composition to indicate a change in condition, such as a change in pH. The color-changing composition includes a matrix-forming component, a colorant, a surfactant and a pH adjuster. The pH adjuster includes a low molecular weight organic acid and a high molecular weight organic acid.

27 Claims, No Drawings

MULTIPLE COMPONENT MATERIALS HAVING A COLOR-CHANGING COMPOSITION

This application is a continuation-in-part application claiming priority from presently copending U.S. application Ser. No. 12/503,364 entitled "Multiple Component Materials Having A Color-Changing Composition" filed on Jul. 15, 2009 now abandoned, in the names of JunMo Gil et al. and Ser. No. 12/503,380 entitled "Multiple Component Materials Having A Color-Changing Composition" filed on Jul. 15, 2009 now abandoned, in the names of SeungRim Yang et al.

FIELD OF THE INVENTION

The present invention relates to multiple-component materials that include a substrate and a printed layer formed on the substrate. The printed layer includes a color-changing composition. The color-changing composition can cause the printed layer to change in appearance of its color when the printed layer is exposed to a change in physical or chemical environment. For example, the printed layer may be on a nonwoven material that is used as a component of an absorbent article. The color-changing composition may include a pH indicator that changes color in response to the presence of urine.

BACKGROUND OF THE INVENTION

Many products, including consumer and professional products, are more effectively used by an end user when they include a feature that indicates a particular condition or degree of use. An example of a visual indicator is a color indicator. Color indicators can either indicate a change in condition or a degree of use through a change from "no color" to "color" (or vice versa) or through a change from one color to a different color.

Exemplary conditions that could be monitored using a color indicator include physical conditions such as the presence of moisture and chemical conditions such as a change in pH. Exemplary consumer products that could be more effective and deliver more benefits to end users by incorporating a suitable color indicator include absorbent articles, facial tissues, bath tissue, paper towels, household cleaning items and personal cleaning wipes. Exemplary professional products that could be more effective and deliver more benefits to end users by incorporating a suitable color indicator include products for medical use, safety garments, industrial cleaning products and nonwoven materials.

Color indicators are well known and are available in various forms. Desirable performance attributes include durability and good retention (i.e. the color indicator remains where intended and does not leach out into other components of the product within which it is being used). Depending on the product application, it may also be desirable to have the structure in which the color indicator is used be wettable, but water insoluble. For purposes of applying the color indicator to a component of a product, it may also be desirable to have a color indicator that can be applied in liquid form at room temperature. When the color indicator is in a liquid form at room temperature, the color indicator can be easily printed (just like an ink composition) onto the desired component of a product.

Examples of how color indicators are already incorporated into consumer products include diapers that have wetness sensors. Some of the wetness sensors used in diapers change color to indicate wetness while others lose color in response to wetness (i.e. the color fades or disappears when it is dissolved by water). The concept of incorporating a color-changing composition into a wearable article (such as a disposable diaper) is known in the art. For example, U.S. Pat. No. 7,159,532 issued to Klofta et al. (hereinafter "the '532 patent") is directed to wetness indicating compositions having improved colorant retention and durability for use with wearable articles. The wetness indicating compositions of the '532 patent have a first binding agent and a second binding agent. The first binding agent immobilizes a colorant when the colorant is in its initial color state and the second binding agent immobilizes the colorant when the colorant is in its final color state. The component materials used in the examples provided in the '532 patent are solid at room temperature as indicated by the description that they need to be melted in order to combine them. While the wetness indicating compositions of the '532 patent are capable of changing color in response to a stimulus, they are not capable of being applied to an article in liquid form at room temperature.

While the color-changing compositions known in the art provide certain benefits, there remains a need for a composition that can be printed on a substrate. There also remains a need for a composition that is durable, has good retention and that shows rapid and dramatic color change when the composition is used in a product. When the purpose of the composition is to detect the presence of wetness, there remains a need for a composition that is water-resistant and water-insoluble. Further, there remains a need for a composition that can be applied, such as by printing, at room temperature so that the composition can be applied to a substrate without heating. In addition to the needs identified above, there are unmet needs associated with using multi-component materials as components of personal care absorbent articles, such as disposable diapers. In particular, there is a need for a color-changing composition that maintains its efficacy when used in conjunction with a breathable outer cover material. Components of breathable outer covers can impact the ability of presently available color indicators to change color in response to the article being wetted.

SUMMARY OF THE INVENTION

The present invention is directed to a multiple-component material that includes a printed layer formed on a substrate. The printed layer includes a color-changing composition that changes color when a change in physical or chemical condition is detected. The multiple-component materials of the invention may be used in personal care articles, such as the outer cover component of a disposable diaper or a training pant. The multiple-component materials of the invention may also be used in the construction of feminine care articles. The color-changing composition includes a matrix-forming component, a colorant, a surfactant and a pH adjuster. The matrix-forming component can be a water-insoluble, film-forming polymer or an ink base, such as a flexographic varnish having an organic solvent base. The colorant can be a pH indicator, preferably a charged pH indicator, capable of changing color in response to the presence of a fluid. The surfactant includes a charged surfactant that attracts the colorant or a combination of a charged surfactant that attracts the colorant and a neutral surfactant. The pH adjuster may include a low molecular weight organic acid and a high molecular weight organic acid. When the multiple-component material is used as part of the outer cover component of a disposable diaper, the color-changing composition is in contact with the absorbent core of the diaper where fluid is stored during use. The color-changing composition is fluid at room temperature and may be applied as an ink to the substrate, such as by printing, spraying or stamping. The color-changing composition may be dissolved in an organic solvent that acts as a carrier and later evaporates after the color-changing composition is applied to the printed layer or forms the printed layer itself.

The matrix-forming component of the color-changing composition can include one or more water-insoluble, film-forming polymers and/or one or more ink bases, such as a flexographic varnish having an organic solvent base. In part, the function of the matrix-forming component is to keep the surfactant, colorant and pH adjuster in proximity to each other. The water-insoluble, film-forming polymer may be selected from acrylate/acrylamide copolymers, polyurethane adhesives, methylcellulose and copolymers of vinylpyrrolidone and dimethylaminopropyl methacrylamide. Benefits of the color-changing composition including a film-forming polymer include that the composition adheres effectively to the substrate which prevents the composition from cracking off of the substrate when the composition is dry.

The matrix-forming component may also or alternatively include an ink base material. The ink base material may include a small molecule, a polymeric material or a mixture of small molecules and polymers. Examples of suitable small molecule base materials include glycols, including triglycerols and their derivatives. Examples of suitable polymeric materials that may be used as ink base materials include polyvinyl alcohol, polyvinyl pyrrolidone, polyethylene glycol, water-insoluble derivatives of polyacrylates and polyacrylamides, poly(hydroxyethyl methacrylates), poly(hydroxylethyl acrylates), carboxymethyl cellulose, gelatin and gum Arabic. Another suitable ink base material for the color-changing compositions of the invention is a flexographic varnish base such as a nitrocellulose compound based varnish or a phenolic-modified co-solvent-type polyamide resin-based varnish. It is believed that the ink base material may help the stability of the color-changing composition. It is also believed that the ink base material may improve the adhesion of the color-changing composition to the substrate of the multiple-component material. The ink base material may be water-insoluble.

When the multi-component material is used as part of the outer cover component of a disposable diaper, the printed layer may have a barrier effect and may contribute to keeping fluid contained within the absorbent core of the diaper. The surfactant of the color-changing composition may be either a charged surfactant that attracts the colorant or a combination of a charged surfactant that attracts the colorant and a neutral surfactant. When the surfactant is charged, the surfactant increases the wettability of the color-changing composition and helps reduce the leaching of the oppositely-charged colorant. The colorant may be a pH indicator where the pH indicator is selected from bromocresol green, bromophenol blue and bromochlorophenol blue. The colorant may be selected so that it responds by changing color to a particular physical or chemical condition. If a charged colorant and an oppositely charged surfactant are used (because the colorant is bound to the surfactant), the colorant is stabilized and is less likely to leach away from the color-changing composition. The color-changing composition may include one or more colorants. When more than one charged colorant is used, the charged colorants may be selected based on the desired effect (e.g. different color, better visibility, etc.). The colorant may include a polymeric colorant. The polymeric colorant can be a charged and/or neutral polymeric pH indicator.

A possible execution of the present invention includes a substrate that is a breathable outer cover of an absorbent article where the breathable outer cover includes calcium carbonate. For such executions, the pH adjuster includes from 1% to 20% of a low molecular weight organic acid and from 1% to 20% of a high molecular weight organic acid. It is believed that the combination of low molecular weight and high molecular weight organic acids prevents premature color change by the charged colorant caused by contact with the calcium carbonate in the breathable outer cover. The pH adjuster may include a ratio of 0.02 to 50 of low molecular weight organic acid to high molecular weight organic acid.

Depending on the type of product that the multiple-component material is incorporated into, the printed layer may be uniform across the substrate or the printed layer may be formed in a pattern. If the color-changing composition is incorporated into an existing printed layer, the color-changing composition may be applied uniformly or it may be applied in a pattern. Whether formed by the color-changing compositions of the inventions or whether formed by another material, the printed layer may be formed on the substrate in one or more patterns selected from stripes, dots, geometric shapes, irregular shapes, alpha-numeric characters, anthropomorphic images, pictorial representation of animals, pictorial representation of inanimate objects, cartoon characters, logos and trademarks.

In another aspect, the present invention is directed to a multiple-component material that includes a substrate and a printed layer on the substrate. The printed layer includes a color-changing composition that includes 20% to 95% of a matrix-forming component; 0.1% to 10% of a colorant; 2% to 50% of a surfactant; and 0.1% to 20% of a pH adjuster, wherein the pH adjuster includes a low molecular weight organic acid and a high molecular weight organic acid. Similarly, in another aspect, the present invention is directed to a disposable absorbent article including a multiple-component material. The multiple-component material includes a substrate and a printed layer on the substrate. The printed layer includes a color-changing composition that includes 20% to 90% of a matrix-forming component; 0.5% to 5% of a colorant; 10% to 30% of a surfactant; and 0.5% to 5% of a pH adjuster, wherein the pH adjuster includes a low molecular weight organic acid and a high molecular weight organic acid.

In a different aspect, the present invention is directed to a method of forming a multiple-component material. The method includes a step of mixing the components of a color-changing composition with an organic solvent to form a mixture. The color-changing composition includes a matrix-forming component; a colorant; a surfactant and a pH adjuster. The pH adjuster includes a low molecular weight organic acid and a high molecular weight organic acid. The method also includes a step of applying the mixture to a substrate. After the applying step, the method includes a step of allowing the mixture to dry; during this step of allowing the mixture to dry, the organic solvent evaporates and the color-changing composition of the mixture forms a film on the substrate. Therefore, the presence of the organic solvent is to facilitate the step of applying the mixture to a substrate. The organic solvent does not remain with the color-changing composition after the mixture dries as a film on the substrate. The method of the invention is more efficient and lower cost than known methods because the mixture can be applied to the substrate at room temperature and without heating because the mixture is liquid at room temperature.

These aspects and additional aspects of the invention will be described in greater detail herein. Further, it is to be understood that both the foregoing general description and the following detailed description are exemplary and are intended to provide further explanation of the invention claimed.

DETAILED DESCRIPTION OF THE INVENTION

The present disclosure of the invention will be expressed in terms of its various components, elements, constructions, configurations, arrangements and other features that may also be individually or collectively be referenced by the term, "embodiment(s)" of the invention, or other similar terms. It is contemplated that the various forms of the disclosed invention may incorporate one or more of its various features and embodiments, and that such features and embodiments may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The present invention relates to multiple-component materials that include a color-changing composition. Unlike prior art color-changing compositions, the color-changing compositions of the present invention are fluid at room temperature and can be applied to a substrate without heating. For example, the color-changing composition may be printed like an ink onto a substrate at room temperature. This feature of the color-changing compositions makes them easier to handle during the manufacture of the articles to which they are applied. Further, the color-changing compositions of the present invention form a film-like layer when they are applied, such as by printing, to a substrate and dried. A benefit of the color-changing composition forming a film on the substrate is to afford good adherence and to prevent cracking.

The color-changing compositions of the invention may include an organic solvent as a vehicle for the compositions to be applied to a substrate where the organic solvent evaporates after application. When in the form of a film layer on a substrate, the color-changing compositions of the invention are wettable but insoluble in water. This feature makes the color-changing compositions desirable for use in articles where the compositions will be exposed to wetness. The feature also results in color-changing compositions that are durable and that are resistant to leaching out of the film-like printed layer. The printed layer may be formed on the substrate in a desired pattern including stripes, dots, geometric shapes and irregular shapes and combinations of such pattern elements. The printed layer may also be formed on the substrate as an alpha-numeric character, an anthropomorphic image, a pictorial representation of an animal, a pictorial representation of an inanimate object, a cartoon character, a product or company logo and a trademark or brand or combinations of such pictorial elements.

The present invention is directed to a multiple-component material that includes a substrate and a printed layer. The substrate may be in the form of a porous foam, a reticulated foam, cellulose tissues, a plastic film, a woven material or a nonwoven material. Suitable plastic films that may be used to form the substrate include polyethylene films and polypropylene films. Suitable woven materials include woven materials made from natural fibers, synthetic fibers or combinations of natural and synthetic fibers. Natural fibers include cotton, silk and wool fibers and synthetic fibers include polyester, polyethylene and polypropylene fibers. Suitable nonwoven materials include nonwoven materials made through traditional techniques such as spunbond, meltblown and bonded carded web materials. The spunbond, meltblown and bonded carded web materials may be made from suitable synthetic fibers such as polyester, polyethylene and polypropylene fibers. The substrate may include combinations of the materials identified above such as a substrate that includes both a porous foam and a nonwoven material or a substrate that includes both a plastic film and a nonwoven material.

The multiple-component materials of the invention also include a printed layer that is adhered to the substrate. The printed layer includes a color-changing composition. The color-changing composition includes a matrix-forming component. The printed layer may be formed by the color-changing composition itself or the color-changing composition may be applied to or incorporated into the printed layer. Because the color-changing compositions of the invention are fluid at room temperature, they can be applied through printing or stamping either directly onto the substrate (thereby self-forming the printed layer) or onto a pre-existing layer having a film-like structure and associated with the substrate.

The color-changing composition includes a matrix-forming component. The matrix-forming component may include one or more water-insoluble, film-forming polymers and/or one or more ink base materials. The matrix-forming component of the color-changing composition forms the medium to keep the colorant, the surfactant and pH adjuster in proximity to each other. By forming the medium, the matrix-forming component enables the performance of the color-changing composition to be wettable, but water-insoluble; and to remain as a film layer on the substrate as opposed to migrating/leaching away from the substrate. The water-insoluble, film-forming polymers are solid at room temperature, but soluble in a volatile organic solvent or an organic mixing solvent so that when used, the color-changing composition is liquid at room temperature. The ink base materials are liquid at room temperature. When an ink base material is included in the matrix-forming component, a volatile organic solvent may or may not be used. Desirably, the water-insoluble, film-forming polymers/copolymers have a substantial amount, greater than about 0.5% by weight, of polar atoms such as oxygen and nitrogen. The polar atoms may be present in polar functional groups such as amides, carboxylic acids and esters. Preferably, the water-insoluble polymers/copolymers are soluble in a volatile organic solvent such as ethanol, acetone, methanol, acetonitrile, tetrahydrofuran, benzene, toluene and mixtures of such solvents. The water-insoluble, film-forming polymer and the other components of the color-changing composition can be dissolved in the organic solvent prior to application onto the substrate. When the mixture of the color-changing composition and the organic solvent is formed, the mixture is liquid at room temperature. The volatile organic solvent evaporates when the color-changing composition is either applied to the printed layer or forms the printed layer.

The color-changing compositions of the invention include a matrix-forming component in an amount of from 20% to 95% of the total weight of the color-changing composition. Desirably, the color-changing compositions of the invention include a matrix-forming component in an amount of from 20% to 90% of the total weight of the color-changing composition.

Suitable water-insoluble, film-forming polymers include acrylate/acrylamide copolymers, polyurethane adhesives, copolymers of vinylpyrrolidone and copolymers of dimethyl aminopropyl methacrylamide. Commercially-available suitable polymers include DERMACRYL 79 polymer and AMPHOMER HC polymer, both of which are acrylate/octylacrylamide copolymers available from Akzo Nobel. Another example of a commercially-available suitable polymer is GANTREZ SP polymer, which is a monoalkyl ester of poly (methyl vinyl ether/maleic acid) copolymer available from International Specialty Products Inc.

Suitable ink base materials may be small molecules, polymeric materials or a mixture of small molecules and polymers. Examples of suitable small molecule base materials include glycols, including triglycerols and their derivatives. Examples of suitable polymeric materials that may be used as ink base materials include polyvinyl alcohol, polyvinyl pyrrolidone, polyethylene glycol, water-soluble derivatives of polyacrylates and polyacrylamides, poly(hydroxyethyl methacrylates), poly(hydroxylethyl acrylates), carboxymethyl cellulose, gelatin and gum Arabic. Another suitable ink base material for the color-changing compositions of the invention is a varnish base such as a nitrocellulose compound based varnish or a phenolic-modified co-solvent-type polyamide resin-based varnish. Further, the ink base material can be a flexographic varnish having an organic solvent base. It is believed that the ink base material may help the stability of the color-changing composition. It is also believed that the ink base material may improve the adhesion of the color-changing composition to the substrate of the multiple-component material. The ink base material may be water-soluble or water-insoluble.

The color-changing composition of the invention also includes a colorant, preferably a charged colorant, that functionally acts as a pH indicator. The colorant may be a neutral pH indicator, a charged pH indicator or a zwitterionic pH indicator. The colorant desirably changes color at either a pH greater than 9.5 or a pH lower than 5.5. The color change may be from color to colorless, colorless to color or from one color to another color. The charged colorant has the charged functional groups either in the core chromophore structure or derivatized in pendent groups. The colorant may be derivatized as a polymer. Examples of suitable colorants include the following: gentian violet (methyl violet), leucomalachite green, methyl yellow, bromophenol blue, Congo red, methyl orange, malachite green, brillian green, crystal violet, erythrosin B, methyl green, methyl violet 2B, picric acid, napthol yellow S, quinaldine red, Eosin Y, basic fuchsin, 4-(p-anilinophenylazo)benzene-sulfonic acid, sodium salt, phloxine B, bromochlorophenol blue W.S., ethyl orange, bromocresol nile blue A, thymolphthalein, aniline blue W.S., alizarin yellow GG, morgant orange I, tropaeolin O, orange G, acid fuchsin, thiazol yellow G, indigo carmine, phenolphthalein, thymolphthalein, alizarine yellow R, bromocresol green and their respective derivatives. The color-changing compositions of the invention include a colorant in an amount of from 0.1% to 10% of the total weight of the color-changing composition. Desirably, the color-changing compositions of the invention include a colorant in an amount of from 0.5% to 5% of the total weight of the color-changing composition. The color-changing compositions of the invention may include more than one colorant. One or more colorants that have visually different colors may be combined or colorants having the same visual color may be combined.

The color-changing composition of the invention may also include a surfactant, preferably oppositely-charged surfactant that attracts the positively or negatively charged colorant. The surfactant may also include a neutral surfactant. It is believed that the surfactant serves a dual role in the color-changing composition. In one regard, the surfactant adjusts the wettability of the composition so that fluids, like urine, can penetrate the composition to change the pH, resulting in a change of the color of the colorant. In a second regard, the surfactant component forms a charge/charge complex with a colorant so that the colorant is imbedded in the composition with minimal leaching. One dimension of the performance of the color-changing compositions of the invention is their response time. Response time can be improved by increasing the wettability of the color-changing composition (by increasing the amount of surfactant) so that fluids can penetrate more rapidly. However, a potential downside of increasing the amount of surfactant is a reduction in stability—particularly at elevated temperature and humidity conditions. Including a neutral surfactant can increase wettability without affecting the stability of the color-changing composition. Therefore, using both neutral surfactants and charged surfactants in the composition can result in compositions with improved wettability and good stability.

The surfactant may be a small molecule or a polymer. Suitable positively charged surfactants include benzathonium chloride and benzethonium chloride. Mixtures of positively charged surfactants may also be used. Suitable negatively charged surfactants include alkyl sulfates such as sodium laurylsulfate, sodium dodecylsulfate and sodium tetradodecyl sulfate. Alkylbenenesulfates such as sodium dodecylbenzenesulfonate and sodium diheptylsulocuccinate are suitable negatively charged surfactants. Additional suitable negatively charged surfactants include dodecyltrimethyl ammonium chloride, stearateamine acetate, sodium polyoxyethyleneakyl ether sulfate and triethanolamine poly oxyethylenealkyl ether sulfate. Mixtures of negatively charged surfactants may also be used.

In addition to charged surfactants, the color-changing composition may include a neutral surfactant. It is believed that the addition of a neutral surfactant to the color-changing composition will improve response speed by increasing the wettability of the color-changing composition. Using both the charged surfactants and a neutral surfactant improves response speed while maintaining the stability of the color-changing composition, particularly under high temperature and high humidity conditions. Suitable neutral surfactants include Tween 20, Tween 40, Tween 80, Triton-X-100, polyethylene lauryl ether, polyoxyethylene nonyl phenyl ether, polyoxyethylene oleyl phenyl ether, polyoxyethylene sorbitan monolaurate, polyethylene glycol monostearate, polyethylene glycol sorbitan monolaurate, polyoxyethylenesorbitan monopalmitate, polyoxyethylenesorbitan monostearate, polyoxyethylenesorbitan monooleate, polyoxyethylenesorbitan trioleate, polypropylene glycol sorbitan monolaurate, polyoxypropylenesorbitan monopalmitate, polyoxypropylenesorbitan monostearate, polyoxypropylenesorbitan monooleate, polyoxypropylenesorbitan trioleate, polyalkyne glycol sorbitan monolaurate, polyalkyne glycol sorbitan monopalmitate, polyalkyne glycol sorbitan monostearate, polyalkyne glycol sorbitan monooleate, polyalkyne glycol sorbitan trioleate and mixtures of such neutral surfactants.

The color-changing compositions of the invention include surfactants in an amount of from 2% to 50% of the total weight of the color-changing composition. Desirably, the color-changing compositions of the invention include oppositely-charged surfactants in an amount of from 10% to 30% of the total weight of the color-changing composition. With regard to the relative amounts of the different types of surfactants, the ratio of charged surfactant to neutral surfactant can range from 0.2 to 10.

In addition to the other components, the color-changing composition includes a pH adjuster. The pH adjuster is any molecule or composition that may be used to control the pH of the color-changing composition. The pH adjuster may be an acid, a base or a combination of both such as would be found with a buffering composition. The pH adjuster is selected in conjunction with the choice of colorant to be used in the color-changing composition. For example, if the color-changing composition includes a colorant that has a color transition point that occurs at a pH of lower than 5.5, the selected pH adjuster is desirably an acid to make the pH of the color-changing composition acidic. If the color-changing composition includes a colorant that transitions color at a pH higher than 9.5, the selected pH adjuster is desirably a base to make the pH of the color-changing composition basic.

When the substrate and printed layer combination of the multiple-component materials of the invention are used as part of the outer cover of an absorbent article, the pH adjuster component provides additional functionality. Absorbent articles having breathable and highly-breathable outer covers (that have the effect of drawing moisture and humidity away from the wearer's skin) have been commercially successful. The water-impermeable, film portion of the outer cover can be made "breathable" through incorporation of particles of calcium carbonate. When used in conjunction with a breathable outer cover material, the color-changing compositions of the invention desirably include a combination of a low molecular weight organic acid and a high molecular weight organic acid to prevent premature "activation" or a change in color by the colorant. When such a combination is used as the pH adjuster, migration of the acids into the outer cover film is mitigated, thereby preventing the premature activation of the colorant caused by a neutralization reaction between the acid and the calcium carbonate particles. The combination of a low molecular weight organic acid and a high molecular weight organic acid provides the best results; when a high molecular weight organic acid completely replaces the low molecular weight organic acid, the response time of the color-changing composition is relatively slower and the color contrast is not optimal. The low molecular weight organic acid typically has a molecular weight less than 1000 Daltons. The high molecular weight organic acid typically has a molecular weight greater than 1000 Daltons.

Examples of suitable acid pH adjusters include organic acids, inorganic acids and polymeric acids; more specifically, examples of low molecular weight organic acids include glycolic acid, citric acid, lactic acid, ascorbic acid, oxalic acid, maleic acid, tartaric acid, salicylic acid, palmitic acid and stearic acid. Examples of high molecular weight organic acids include polyacrylic acids, polymethacrylic acids and copolymers containing acrylic acids, methacrylic acids or both acrylic acids and methacrylic acids.

Both the low molecular weight acids and the high molecular weight acids can be "polymeric". Depending on the number of monomer units, the polymeric acid will either be low molecular weight (typically less than 1000 Daltons) or high molecular weight (typically greater than 1000 Daltons). The low molecular weight organic acids having repeating monomer units may be referred to as oligomers. In some aspects, the polymeric acid can be a "bidentate" or higher order acid. By "bidentate or higher order" it is meant that the polymeric acid has more than one acid group in its smallest polymer building block. This can be easily understood when one compares ascorbic acid to tartronic acid (two acid groups) and citric acid (three acid groups). In some aspects, the polymeric acids may be a dendrimer or the like where the dendrimer's surface and interior are fully functionalized with acid groups. Examples of suitable, simple polymeric acids for which the number of repeating monomer units can vary are salicylic acid and ascorbic acid; if the molecular weight is less than 1000 Daltons, the acid may be referred to as an oligomer and if the molecular weight is greater than 1000 Daltons, the acid may be referred to as a polymer. The following are examples of suitable dicarboxylic polymeric acids:

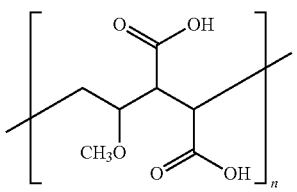

Poly(methyl vinyl ether-alt-maleic acid) average $M_w$ ~216,000 by LS, average $M_n$ ~80,000, powder

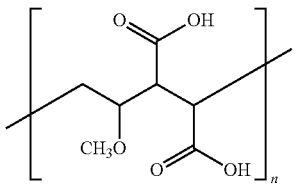

Poly(methyl vinyl ether-alt-maleic acid) average $M_w$ ~1,980,000 by LS, average $M_n$ ~960,000, powder Examples of suitable tricarboxylic polymeric acids include the following:

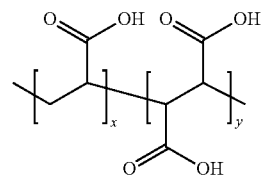

Poly(acrylic acid-co-maleic acid) solution average $M_w$ 3,000, 50 wt. % in $H_2O$ Examples of suitable polyacrylic acids include the following: polyacrylic acid having an average molecular weight of about 1800 Daltons, polyacrylic acid having an average molecular weight of about 450,000 Daltons, polyacrylic acid having an average molecular weight of about 1,250,000 Daltons and polyacrylic acid having an average molecular weight of about 3,000,000 Daltons. An example of a suitable, strong polymeric acid is Poly(vinylphosphonic acid).

Examples of suitable basic pH adjusters include organic bases, inorganic bases and polymeric bases; more specifically, examples include sodium hydroxide, sodium carbonate, sodium bicarbonate, sodium borate, potassium hydroxide, polymeric amines, dendrimeric amine and 1,3-pentanediamine. Combination pH adjusters that have a buffering effect include acetic buffer, borate buffer and carbonate buffer. Desirably, the pH of the combination pH adjuster is either greater than 10 or lower than 5. Typically, the combination pH adjuster is in solution form and the concentration of the buffer may range from about 0.01 milliMolar to about 1000 milliMolar and desirably range from about 1 milliMolar to about 20 milliMolar, depending on the combination pH adjuster selected. The color-changing compositions of the invention include a pH adjuster in an amount of from 0.1% to 20% of the total weight of the color-changing composition. Desirably, the color-changing compositions of the invention include a pH adjuster in an amount of from 0.5 to 5% of the total weight of the color-changing composition. With respect to the relative amounts of organic acid, the ratio of low molecular weight organic acid to high molecular weight organic acid can range from 0.02 to 50.

Benefits of the pH adjuster include stabilizing the colorant against premature color changes that may be caused by exposure to humid environments. For example, the pH adjuster is believed to maintain a stable pH, such as a low pH environment with an acidic pH adjuster, around the colorant even when the film layer is exposed to high humidities.

When the components of the color-changing composition are formed as a printed layer on the substrate, they can be dissolved or suspended in an organic solvent that later evaporates. The result of the color-changing composition forming a printed layer on the substrate is the multiple-component material of the invention. The organic solvent may be a single solvent or a mixture of solvents. Suitable solvents to carry the color-changing composition include ethanol, isopropanol, acetone, methanol, acetonitrile, tetrahydrofuran, benzene and toluene. An example of a useful application of the present invention is to apply the color-changing composition to a nonwoven substrate that is used as a component of a disposable absorbent article. More specifically, the nonwoven substrate may be a spunbond or other nonwoven material that is used to form the outer cover of a disposable diaper. The substrate may also be a polyethylene film that is adhered to a nonwoven material to form the outer cover of a disposable diaper. The printed layer of the present invention may be formed on a nonwoven substrate or on a film. Because the color-changing compositions of the present invention are fluid at room temperature, they can be easily applied through printing to a substrate. Because the outer cover of an absorbent article, such as a disposable diaper, is typically adjacent the absorbent structure of the article, the color-changing composition is applied to a component that is in proximity to the absorbent structure when the finished product is in use. Therefore, the color-changing composition can be used to indicate a change in condition of the absorbent structure, such as wetness.

An example of a color-changing composition of the invention is a composition that includes an acrylate and octylacrylamide copolymer system as the water-insoluble, film-forming polymer; this polymer can assist adhesion of the colorant to the substrate and provide wettability with water resistance. Another example of the color-changing composition of the invention is a composition that includes a polyurethane adhesive with amide functionality as the water-insoluble, film-forming polymer. This water-insoluble, film-forming polymer can be dissolved in an alcohol for application to the substrate (with the alcohol subsequently evaporating). The color-changing compositions of the invention are water-wettable to allow rapid color change of the colorant component, but are water-insoluble to prevent leaching of the colorant. These are desirable performance attributes.

The following are various examples that illustrate aspects of the present invention:

Preparation of Exemplary Color-Changing Composition and Multiple-Component Material #1:

A color-changing composition that is an example of the present invention includes a matrix-forming component of a flexographic varnish having an organic solvent base in an amount of 2.5 ml. The composition also includes a colorant of bromocresol green in an amount of 15 mg/ml and a surfactant of benzethenium chloride in an amount of 20 mg/ml. The composition includes a pH adjuster of a low molecular weight organic acid, citric acid, in an amount of 200 mg/ml and high molecular weight organic acid, polyacrylic acid, in an amount of 200 mg/ml. The colorant, surfactant and pH adjusters are combined together and dissolved in 3 ml of ethanol. This solution is then mixed with the matrix-forming component by vortex until a homogenous solution is formed.

The multiple-component material was prepared by brushing 250 µl of the color-changing composition on a piece of polypropylene film material (such as would be used to form the outer cover of a disposable absorbent article) using a disposable foam brush to form a thin film. The film was allowed to dry under ambient condition for 2 hours to form a yellow color. To ensure that the color-changing composition was functioning as expected, a drop of water or synthetic urine or real urine sample caused the yellow to blue color within 5 minutes.

Preparation of Exemplary Color-Changing Composition and Multiple-Component Material #2:

A color-changing composition that is an example of the present invention includes a matrix-forming component of a flexographic varnish having an organic solvent base in an amount of 2.5 ml. The composition includes a colorant of bromocresol green in an amount of 15 mg/ml. The composition also includes a surfactant of benzethenium chloride in an amount of 150 mg/ml and a neutral surfactant of Tween 40 in an amount of 50 mg/ml. The composition includes a pH adjuster of a low molecular weight organic acid, citric acid, in an amount of 200 mg/ml and a high molecular weight organic acid, polyacrylic acid, in an amount of 200 mg/ml. The colorant, surfactants and pH adjusters are combined together and dissolved in 3 ml of ethanol. This solution is then mixed with the matrix-forming component by vortex until a homogenous solution is formed.

The multiple-component material was prepared by brushing 250 µl of the color-changing composition on a piece of polypropylene film material (such as would be used to form the outer cover of a disposable absorbent article) using a disposable foam brush to form a thin film. The film was allowed to dry under ambient condition for 2 hours to form a yellow color. To ensure that the color-changing composition was functioning as expected, a drop of water or synthetic urine or real urine sample caused the yellow to blue color within 5 minutes.

Stability Testing of Multiple-Component Materials and Color-Changing Compositions of the Invention In order to evaluate stability, the color-changing compositions were brushed on film materials such as those that would be used as part of the outer cover (e.g., highly breathable films with calcium carbonate) of disposable absorbent articles. The film materials with color-changing compositions were incubated in an oven at 40° C. and 75% humidity over a period of one day to two weeks. The film materials were then taken out once a day to visually compare the resulting color with the original color. The response speed and color change upon contact with synthetic urine or water or real urine samples were also visually examined and compared qualitatively.

Comparison of Stability Between Color-Changing Compositions Having Different Amounts of pH Adjusters Five color-changing compositions were prepared. Each composition contained 2.5 ml of flexographic varnish having an organic solvent base, 200 mg of benzethenium chloride (0.5 ml in ethanol), 15 mg of bromocresol green (0.75 ml) and different amounts of polyacrylic acid (high molecular weight organic acid) and citric acid (low molecular weight organic acid): (1) Sample 1 contained 200 mg polyacrylic acid (1 ml) and 200 mg citric acid (1 ml); (2) Sample 2 contained 300 mg polyacrylic acid (1.5 ml) and 100 mg citric acid (0.5 ml); (3) Sample 3 contained 400 mg polyacrylic acid (2 ml) and 0 mg citric acid (0 ml); (4) Sample 4 contained 0 mg polyacrylic acid (0 ml) and 400 mg citric acid (2 ml); and (5) Sample 5 contained 100 mg polyacrylic acid (0.5 ml) and 300 mg citric acid (1.5 ml). Each sample was brushed on Clopay 1652 polypropylene film and air-dried to form a yellow color. The yellow color changed to blue when wetted with synthetic urine within 10 minutes (similar for each of the samples; some of the samples changed color in less than a minute). As described above, the samples were then incubated in an oven at 40° C. and 75% humidity for two days to compare the stability of the color change without synthetic urine insults. Samples 1, 2, and 5 became less greenish or bluish than samples 3 and 4. Apparently, the compositions with both a high molecular weight organic acid (polyacrylic acid) and a low molecular weight organic acid (citric acid) are more stable (i.e. less likely to experience premature color change under humid conditions) than the compositions with either polyacrylic acid or citric acid.

Comparison of Stability Between Color-Changing Compositions Having Different Surfactants on Highly Breathable Pliant Y Film Four color-changing compositions were prepared. Each composition contained 2.5 ml of flexographic varnish having an organic solvent base, 200 mg of benzethenium chloride (0.5 ml in ethanol), 15 mg of bromocresol green (0.75 ml) and different amounts of polyacrylic acid (high molecular weight organic acid), citric acid (low molecular weight organic acid) and Tween-40 (neutral surfactant): (1) Sample 1 contained 100 mg Tween-40, 100 mg polyacrylic acid (0.5 ml) and 400 mg citric acid (2 ml); (2) Sample 2 contained 100 mg polyacrylic acid (0.5 ml) and 400 mg citric acid (2 ml); (3) Sample 3 contained 100 mg Tween-40, 100 mg polyacrylic acid (0.5 ml) and 300 mg citric acid (1.5 ml); and (4) Sample 4 contained 50 mg Tween-40, 100 mg polyacrylic acid (0.5 ml) and 400 mg citric acid (2 ml). Each sample was brushed on pieces of Pliant Y polypropylene film. The samples were incubated at 40° C. and 75% humidity for two days. While sample 2 (no neutral surfactant) had slightly better stability (i.e. less likely to experience premature color change), samples 1, 3 and 4 had shorter response times and better color contrast than sample 2. The samples having a neutral surfactant, a high molecular weight organic acid (polyacrylic acid) and a low molecular weight organic acid (citric acid) have better overall performance (e.g. response speed, color contrast and good stability) than the sample without a neutral surfactant.

Comparison of Stability Between Color-Changing Compositions Having Different Surfactants on Highly Breathable Clopay 1652 Film Five color-changing compositions were prepared. Each composition contained 2.5 ml of flexographic varnish having an organic solvent base, 200 mg of benzethenium chloride (0.5 ml in ethanol), 15 mg of bromocresol green (0.75 ml) and different amounts of polyacrylic acid (high molecular weight organic acid), citric acid (low molecular weight organic acid) and Tween-40 (neutral surfactant): (1) Sample 1 contained 100 mg Tween-40, 100 mg polyacrylic acid (0.5 ml) and 400 mg citric acid (2 ml); (2) Sample 2 contained 100 mg polyacrylic acid (0.5 ml) and 400 mg citric acid (2 ml); (3) Sample 3 contained 100 mg Tween-40 (0.25 ml), 100 mg polyacrylic acid (0.5 ml) and 300 mg citric acid (1.5 ml); (4) Sample 4 contained 50 mg Tween-40 (0.125 ml), 100 mg polyacrylic acid (0.5 ml) and 400 mg citric acid (2 ml); and (5) Sample 5 contained 100 mg polyacrylic acid (0.5 ml) and 300 mg citric acid (1.5 ml). Each sample was brushed on Clopay 1652 polypropylene film and air-dried to form a yellow color. The yellow color changed to blue when wetted with synthetic urine within 10 minutes (some samples change color in less than a minute). The samples were incubated in an oven of 40° C. and 75% humidity for two days. Although all five samples have similar stability (i.e. likelihood of premature color change), samples 1, 3 and 4 have better response time than samples 2 and 5. Apparently, the presence of a neutral surfactant does not have an adverse effect on stability, yet improves response time. The compositions with a neutral surfactant, a high molecular weight organic acid (polyacrylic acid) and a low molecular weight organic acid (citric acid) have better overall performance (response speed, color contrast and good stability) than compositions without neutral surfactants.

While the multiple-component materials of the invention have been described in detail with respect to specific aspects thereof, it will be appreciated that those skilled in the art, upon attaining an understanding of the foregoing, may readily conceive of alterations to, variations of and equivalents to these materials. Accordingly, the scope of the present invention should be assessed as that of the appended claims and any equivalents thereto.

We claim:

1. A multiple-component material, the material comprising:
   a substrate and a printed layer on the substrate, wherein the printed layer includes a color-changing composition, the color-changing composition comprising:
   a matrix-forming component;
   a colorant;
   a surfactant; and
   a pH adjuster, wherein the pH adjuster includes a low molecular weight organic acid and a high molecular weight organic acid, wherein the low molecular weight organic acid comprises a molecular weight less than 1000 Daltons and the high molecular weight organic acid comprises a molecular weight more than 1000 Daltons and wherein the pH adjuster includes 1-20% of the total weight of the color-changing composition of the low molecular weight organic acid and 1-20% of the total weight of the color-changing composition of the high molecular weight organic acid.

2. The multiple-component material of claim 1, wherein the pH adjuster has a ratio of 0.02 to 50 of low molecular weight organic acid to high molecular weight organic acid.

3. The multiple-component material of claim 1, wherein the low molecular weight organic acid is selected from lactic acid, amino acid, ascorbic acid, glycolic acid, salicylic acid, tartaric acid, citric acid, EDTA, tartronic acid and maleic acid.

4. The multiple-component material of claim 1, wherein the high molecular weight organic acid is selected from polyacrylic acids, polymethacrylic acids and copolymers containing acrylic acids, methacrylic acids or both acrylic acids and methacrylic acids.

5. The multiple-component material of claim 1, wherein the matrix-forming component has greater than 0.5% by weight of polar atoms.

6. The multiple-component material of claim 1, wherein the matrix-forming component is selected from a water-insoluble, film-forming polymer and a flexographic varnish including an organic solvent.

7. The multiple-component material of claim 1, wherein the water-insoluble, film-forming polymer is selected from acrylate/acrylamide copolymers, polyurethane adhesives, methyl cellulose and copolymers of vinylpyrrolidone and dimethylaminopropyl methacrylamide.

8. The multiple-component material of claim 1, wherein the surfactant includes a charged surfactant and a neutral surfactant.

9. The multiple-component material of claim 1, wherein the colorant is a pH indicator.

10. The multiple-component material of claim 1, wherein the colorant is a polymeric colorant.

11. The multiple-component material of claim 9, wherein the pH indicator is selected from bromocresol green, bromophenol blue and bromochlorophenol blue, methyl orange, tetrabromophenol blue, ethyl orange, Congo red, methyl red and allure red AR.

12. The multiple-component material of claim 1, wherein the color-changing composition includes more than one colorant.

13. The multiple-component material of claim 1, wherein the substrate is a non-woven material.

14. The multiple-component material of claim 1, wherein the substrate is a polyolefin film.

15. The multiple-component material of claim 14, wherein the polyolefin film includes calcium carbonate.

16. A disposable absorbent article including the multiple-component material of claim 1 as part of an outer cover.

17. The multiple-component material of claim 1, wherein the printed layer is formed on the substrate in one or more patterns selected from stripes, dots, geometric shapes, irregular shapes, alpha-numeric characters, anthropomorphic images, pictorial representation of animals, pictorial representation of inanimate objects, cartoon characters, logos and trademarks.

18. A multiple-component material, the material comprising:
    a substrate and a printed layer on the substrate, wherein the printed layer includes a color-changing composition, the color-changing composition comprising:
    20% to 95% of the total weight of the color-changing composition of a matrix-forming component;
    2% to 50% of the total weight of the color-changing composition of a surfactant;
    1% to 10% of the total weight of the color-changing composition of a colorant; and
    of a pH adjuster, wherein the pH adjuster includes a low molecular weight organic acid and a high molecular weight organic acid, the low molecular weight organic acid comprises a molecular weight less than 1000 Daltons, and the high molecular weight organic acid comprises a molecular weight more than 1000 Daltons and wherein the pH adjuster includes 1-20% of the total weight of the color-changing composition of the low molecular weight organic acid and 1-20% of the total weight of the color-changing composition of the high molecular weight organic acid.

19. A disposable absorbent article including a multiple-component material, the material comprising: a substrate and a film layer on the substrate, wherein the film layer includes a color-changing composition, the color-changing composition comprising:
    20% to 90% of the total weight of the color-changing composition of a matrix-forming component;
    5% to 5% of the total weight of the color-changing composition of a colorant;
    10% to 30% of the total weight of the color-changing composition of a surfactant; and
    of a pH adjuster, wherein the pH adjuster includes a low molecular weight organic acid and a high molecular weight organic acid, the low molecular weight organic acid comprises a molecular weight less than 1000 Daltons, and the high molecular weight organic acid comprises a molecular weight more than 1000 Daltons and wherein the pH adjuster includes 1-20% of the total weight of the color-changing composition of the low molecular weight organic acid and 1-20% of the total weight of the color-changing composition of the high molecular weight organic acid.

20. A method of forming a multiple-component material, the method comprising the steps of:
    mixing components of a color-changing composition with an organic solvent to form a mixture, wherein the components of the color-changing composition include a matrix-forming component; a colorant; a surfactant; and a pH adjuster, wherein the pH adjuster includes a low molecular weight organic acid and a high molecular weight organic acid, the low molecular weight organic acid comprises a molecular weight less than 1000 Daltons, and the high molecular weight organic acid comprises a molecular weight more than 1000 Daltons and wherein the pH adjuster includes 1-20% of the total weight of the color-changing composition of the low molecular weight organic acid and 1-20% of the total weight of the color-changing composition of the high molecular weight organic acid;
    applying the mixture to a substrate; and
    allowing the mixture to dry, wherein during this step the organic solvent evaporates and the color-changing composition of the mixture forms a film on the substrate.

21. The method of forming a multiple-component material of claim 20, wherein the mixture is liquid at room temperature.

22. A multiple-component material, the material comprising:
    a substrate and a printed layer on the substrate, wherein the printed layer includes a color-changing composition, the color-changing composition comprising:
    a matrix-forming component;
    a charged colorant;
    a charged surfactant, the charged surfactant being oppositely charged from the charged colorant; and
    a pH adjuster, wherein the pH adjuster includes a low molecular weight organic acid and a high molecular weight organic acid, wherein the low molecular weight organic acid comprises a molecular weight less than 1000 Daltons and the high molecular weight organic acid comprises a molecular weight more than 1000 Daltons, and wherein the pH adjuster includes 1-20% of the total weight of the color-changing composition of the low molecular weight organic acid and 1-20% of the total weight of the color-changing composition of the high molecular weight organic acid.

23. The multiple component material of claim 22, wherein the matrix-forming component comprises a water-insoluble, film-forming polymer.

24. The mulitple component material of claim 22, wherein the color-changing composition comprises 2% to 50% of the charged surfactant and 10% to 30% of the charged colorant.

25. A multiple-component material, the material comprising:
    a substrate and a printed layer on the substrate, wherein the film layer includes a color-changing composition, the color-changing composition comprising:
    a matrix-forming component;
    a colorant;
    a charged surfactant;
    a neutral surfactant; and
    a pH adjuster, wherein the pH adjuster includes a low molecular weight organic acid and a high molecular weight organic acid, wherein the low molecular weight organic acid comprises a molecular weight less than 1000 Daltons and the high molecular weight organic acid comprises a molecular weight more than 1000 Daltons, and wherein the pH adjuster includes 1-20% of the total weight of the color-changing composition of the low molecular weight organic acid and 1-20% of the total weight of the color-changing composition of the high molecular weight organic acid.

26. The multiple component material of claim 25, wherein the matrix-forming component comprises a water-insoluble, film-forming polymer.

27. The multiple component material of claim 25, wherein a ratio of the charged surfactant to the neutral surfactant is about 0.2 to about 10.

* * * * *